United States Patent [19]

Landauer

[11] 4,190,600
[45] Feb. 26, 1980

[54] PROCESS FOR THE MANUFACTURE OF M-HALOBENZOYL HALIDES

[75] Inventor: Franz Landauer, Frankfurt am Main, Fed. Rep. of Germany

[73] Assignee: Hoechst Aktiengesellschaft, Frankfurt, Fed. Rep. of Germany

[21] Appl. No.: 944,249

[22] Filed: Sep. 21, 1978

[30] Foreign Application Priority Data

Sep. 24, 1977 [DE] Fed. Rep. of Germany ....... 2743144

[51] Int. Cl.$^2$ ............................................. C07C 63/12
[52] U.S. Cl. ............................................. 260/544 D
[58] Field of Search .................................. 260/544 D

[56] References Cited

U.S. PATENT DOCUMENTS 3,996,274  12/1976  Jurewicz ..................... 260/544 D

OTHER PUBLICATIONS

Friedel–Crafts and Related Reactions, Editor Olah, vol. 1, pp. 214–215, 309–311, 365; vol. III, part 2, pp. 1555–1556, (1963).

*Primary Examiner*—Gerald A. Schwartz
*Attorney, Agent, or Firm*—Curtis, Morris & Safford

[57] ABSTRACT m-Halobenzoyl halides are prepared by chlorinating or brominating benzoyl chloride or benzoyl bromide in the absence of a solvent and in the presence of FeCl$_3$ or FeBr$_3$ as the catalyst and of sulfur and/or at least one inorganic and/or organic sulfur compound as the cocatalyst, at a temperature of from about 0° to 90° C. The compounds are valuable starting products and intermediates for the manufacture of dyestuffs, pharmaceuticals and plant protectives.

13 Claims, No Drawings

PROCESS FOR THE MANUFACTURE OF M-HALOBENZOYL HALIDES

The present invention relates to a process for the manufacture of m-halobenzoyl halides.

m-Halobenzoyl halides are valuable starting compounds and intermediates for the manufacture of dyestuffs, pharmaceuticals and plant protectives. Especially m-chlorobenzoyl chloride is a valuable starting compound for the manufacture of herbicides which are based on halophenoxybenzoic acid, and disclosed in U.S. Pat. No. 3,652,645.

Various processes are known for the manufacture of m-halobenzoyl halides. An advantageous process for the manufacture of m-chlorobenzoyl chloride, for example, consists in chlorinating benzoyl chloride in the absence of a solvent and in the presence of anhydrous $FeCl_3$ as the catalyst and of iodine as the cocatalyst, at a temperature from 0° to 50° C. (cf. German Auslegeschrift No. 2,538,158). It seems, however, that the yields of m-chlorobenzoyl chloride in the range of from about 60 to 66%, calculated on reacted benzoyl chloride, which are achieved according to the examples of this reference are not entirely satisfactory, especially for large-scale requirements and, consequently, should be improved. Furthermore the iodine used as the cocatalyst frequently leads to undesired discolorations of the resulting product.

There was, consequently, a need to modify or improve the above-mentioned process to make sure that higher yields and no discolored products would be obtained. This need could be met a simple and satisfactory manner by using sulfur and/or at least one inorganic and/or organic sulfur compound instead of iodine as the cocatalyst in the process of German Auslegeschrift No. 2,538,158. The process is applicable to the manufacture not only of m-chlorobenzoyl chloride, but also of m-bromobenzoyl bromide, of m-chlorobenzoyl bromide or of m-bromobenzoyl chloride.

The present invention, consequently, relates to a process for the preparation of m-halobenzoyl halides by chlorinating or brominating benzoyl chloride or benzoyl bromide in the absence of a solvent and in the presence of $FeCl_3$ or $FeBr_3$ as the catalyst and of a cocatalyst, at a temperature of from 0° to 90° C., preferably of from about 10° to 75° C., and comprises using as the cocatalyst sulfur and/or at least one inorganic and/or organic sulfur compound.

As mentioned before, it is possible to prepare according to the process of the present invention both m-halobenzoyl halides having the same halogen in the molecule(m-chlorobenzoyl chloride and m-bromobenzoyl bromide) and mixed m-halobenzoyl halides (m-chlorobenzoyl bromide and bromobenzoyl chloride), m-chlorobenzoyl chloride being prepared preferably. $FeCl_3$ is suitably used as catalyst in the chlorination and $FeBr_3$ as catalyst in the bromination; however, on principle, $FeBr_3$ may alternatively be used in the chlorination and $FeCl_3$ in the bromination. When preparing mixed halogen compounds, either $FeCl_3$ or $FeBr_3$ may be used advantageously. If possible, the catalysts should be anhydrous. As the cocatalyst there is used sulfur and/or at least one inorganic and/or organic sulfur compound. Suitable sulfur compounds are in the first place sulfur halides, for example $SCl_2$ and $S_2Cl_2$ or the corresponding bromides, $S_2Cl_2$ and $S_2Br_2$ being used preferably. Advantageously sulfur chloride is used as cocatalyst in the chlorination and sulfur bromide as cocatalyst in the bromination.

Suitable sulfur compounds are especially organic compounds of the bivalent sulfur having one free hydrogen atom at the sulfur atom, for example thioglycolic acid, thioacetic acid, thiophenol etc. However, bivalent organic sulfur compounds without a free hydrogen atom at the sulfur atom, for example thiophene or thiourea may alternatively be used. Sulfur or one of said inorganic or organic sulfur compounds may be used alone or a mixture of said cocatalyst substances may be used. Benzoyl chloride is preferably chorinated in the presence of $FeCl_3$ as a catalyst and sulfur and/or $S_2$ as a cocatalyst.

The catalyst quantity is advantageously in the range from about 0.05 to 2 weight percent, preferably from about 0.1 to 1 weight percent, calculated on benzoyl chloride or benzoyl bromide used as the starting compound.

The cocatalyst should be present suitably in a quantity corresponding to a sulfur content of from about 0.01 to 2 weight percent, preferably from about 0.05 to 0.5 weight percent, calculated on benzoyl chloride or benzoyl bromide used as the starting compound. The chlorine or bromine used for the halogenation may be liquid or gaseous. The reaction may be carried out pressureless, under overpressure or under reduced pressure in known apparatuses, discontinuously or continuously. Naturally care should be taken that no overchlorination or overbromination, or at least no essential overchlorination or over overbromination, occurs, since it will reduce the yield of the desired m-halogen product and, consequently, the profitability of the process.

The yields of m-halobenzoyl halides obtained according to the invention are in the range of from about 75 to 80% and higher of the theoretical yield, calculated on the benzoyl chloride or bromide used as the starting compound. They are, consequently, about at least 10 percent higher than those described in German Auslegeschrift No. 2,538,158. Upon halogenation there are obtained colorless distilled products in the distillation.

It has been proposed to employ Fe-III catalysts and sulfur-containing cocatalysts in the halogenation of aromatic compounds (cf. Australian Pat. No. 223,024; Australian Pat. No. 230,337 and German Auslegeschrift No. 1,543,020). However, these combinations of catalyst and cocatalyst were used exclusively for improving the ratio between p- and o-isomers in the preparation of dichlorobenzene (cf. Australian Pat. No. 223,024; Australian Pat. No. 230,337) and of monochlorotoluene (cf. German Pat. No. 1.543,020). Considering these results, it was suprising and unobvious that the same combination of catalyst and cocatalyst could be used for improving the yields of m-halogen products by halogenation of benzoyl halides.

The following examples illustrate the invention:

EXAMPLE 1

421 g of benzoyl chloride (3 mols) are fed to a four-necked flask equipped with a reflux condenser, a thermometer and a gas inlet. Upon addition of 1.8 g of iron-III chloride (corresponding to 0.43 percent of the weight of benzoyl chloride used) and 0.9 g of powdered sulfur (corresponding to 0.21 percent of the weight of benzoyl chloride used), there are introduced 160 g of chlorine (2.25 mols) at a temperature of from 30° to 35° C., for a period of 3 hours.

After having blown off the hydrogen chloride with nitrogen, the chlorination mixture is distilled off from the catalyst, the boiling range in vacuo (7 mm Hg) being of from 60° to 93° C. 490 g of distillate are obtained.

According to gas chromatographic analysis, the resulting product has the following composition:

|  | weight percent | g | mol |
|---|---|---|---|
| benzoyl chloride | 35.5 | 174.2 | 1.24 |
| m-Cl " | 49.3 | 241.5 | 1.38 |
| p-Cl " | 1.0 | 4.9 | 0.03 |
| q-Cl " | 6.2 | 30.5 | 0.17 |
| di-Cl " | 7.7 | 37.8 | 0.18 |

It can be deduced from the above table that 1.38 mols of the desired m-chlorinated compound are obtained from 1.76 mols of consumed benzoyl chloride, which corresponds to a yield of 78.4 percent of the theoretical yield.

The same yield is obtained when performing the chlorination at a temperature of from 20° to 25° C.

EXAMPLE 2

400 g (2.85 mols) of benzoyl chloride are placed into the same apparatus as in Example 1 and upon addition of 1.8 g of iron-III chloride and 1.1 g of thioglycolic acid, the batch is chlorinated at 35° C., while introducing 110 g of chlorine (1.55 mols) in the course of 2 hours. After having blown off the hydrogen chloride with nitrogen, the chlorination mixture is purified from the catalysts in vacuo by distillation. The boiling range goes from 92° to 125° C. (at 27 mm Hg). 431 g of distillate are obtained.

The gas chromatographic analysis reveals the following composition of the resulting product:

|  | weight percent | g | mol |
|---|---|---|---|
| benzoyl chloride | 50 | 215.6 | 1.53 |
| m-Cl-benzoyl chloride | 39 | 168 | 0.96 |
| p-Cl-benzoyl chloride | 0.9 | 3.4 | 0.02 |
| O-Cl-benzoyl chloride | 6.1 | 26.3 | 0.15 |
| di-Cl-benzoyl chloride | 5.9 | 25.4 | 0.12 |

This signifies that 168 g of m-chlorobenzoyl chloride (0.96 mol) are obtained from 1.32 mols of consumed benzoyl chloride, which corresponds to a yield of 73% of the theoretical yield.

EXAMPLE 3

393 g of benzoyl chloride (2.8 mols) are placed into the apparatus of Example 1, 1.7 g of FeCl$_3$ (0.43 weight percent) and 1.68 g of disulfur dichloride (0.43 weight percent or 0.2 weight percent of sulfur) are added thereto, while 130 g of chlorine (1.83 mols) are introduced for 2 hours, at a temperature of from 30° to 40° C. After having blown off the hydrogen chloride, the chlorination product is distilled off, whereby the desired product boils off at a temperature of from 96° to 130° C. (at 27 mm Hg). 443 g of distillate are obtained.

The gas chromatographic analysis reveals the following composition:

|  | weight percent | g | mol |
|---|---|---|---|
| benzoyl chloride | 42 | 186 | 1.31 |
| m-Cl- " " | 45 | 199.4 | 1.14 |
| p-Cl- " " | 1.0 | 4.4 | 0.03 |
| o-Cl- " " | 6.2 | 27.4 | 0.16 |
| di-Cl- " " | 5 | 22.2 | 0.10 |

The yield of m-chlorobenzoyl chloride is, consequently, 76.5% of the theoretical yield, calculated on reacted benzoyl chloride.

EXAMPLE 4

281 g of benzoyl chloride (2 mols), 2.5 g of iron-III chloride (0.9%) and 1.5 g of pulverulent sulfur (0.53 percent) are introduced into a four-necked flask equipped with a reflux condenser, a thermometer and a dripping funnel. In the course of 4.5 hours, 100 g of bromine (0.63 mol) are added dropwise, at a temperature of from 70° to 75° C. After having blown off the hydrogen bromide, the resulting mixture is separated from the catalysts by distillation in vacuo. 325 g of substance distill over at a temperature of from 95° to 145° C. (at 27 mm Hg). According to the gas chromatographic analysis, the product has the following composition:

|  | weight percent | g | mol |
|---|---|---|---|
| benzoyl chloride | 69 | 224.3 | 1.60 |
| m-bromo- " " | 30 | 97.5 | 0.44 |
| p-bromo- " " | 0.4 | 1.3 | 0.006 |
| o-bromo- " " | 0.4 | 1.3 | 0.006 |

The yield of m-bromobenzoyl chloride is, consequently, practically quantitative, calculated on reacted benzoyl chloride.

What is claimed is:

1. In a process for the preparation of m-halobenzoyl halides by chlorinating or brominating benzoyl chloride or benzoyl bromide in the absence of a solvent and in the presence of a catalyst and a cocatalyst, at a temperature of from about 0° to 90° C., the improvement comprising using as the catalyst FeCl$_3$ or FeBr$_3$ and as the cocatalyst sulfur, a sulfur halide, thioglycolic acid, thioacetic acid, thiphenol, thiophene, thiourea, or mixtures thereof.

2. The process as claimed in claim 1, wherein benzoyl chloride is chlorinated in the presence of FeCl$_3$ as the catalyst and sulfur and/or S$_2$Cl$_2$ as the cocatalyst.

3. The process as claimed in claims 1 or 2, wherein the improvement further comprises using the catalyst in an amount of from about 0.05 to 2 weight percent, calculated on benzoyl chloride or benzoyl bromide used as the starting compound.

4. The process as claimed in claims 1 or 2, wherein the cocatalyst is used in an amount corresponding to a sulfur content of from about 0.01 to 2 weight percent, calculated on benzoyl chloride or benzoyl bromide used as the starting compound.

5. The process, as claimed in claim 3, wherein the catalyst is used in an amount of from about 0.1 to 1 weight percent.

6. The process, as claimed in claim 4, wherein the cocatalyst is used in an amount corresponding to a sulfur content of from about 0.05 to 0.5 weight percent.

7. The process, as claimed in claim 1, wherein the cocatalyst is thioglycolic acid, thioacetic acid, or thiophenol.

8. The process, as claimed in claim 1, wherein the cocatalyst is thiophene or thiourea.

9. The process, as claimed in claim 1, wherein the cocatalyst is sulfur or a sulfur halide.

10. The process, as claimed in claim 9, wherein the cocatalyst is $SCl_2$, $S_2CL_2$, $SBr_2$ or $S_2Br_2$.

11. The process, as claimed in claim 1, wherein the cocatalyst is powdered sulfur.

12. In a process for the preparation of m-chlorobenzoyl chloride by chlorinating benzoyl chloride in the absence of a solvent and in the presence of a catalyst and of a cocatalyst at a temperature of from about 0° to 90° C., the improvement comprising using as the cocatalyst $S_2Cl_2$ in an amount corresponding to a sulfur content of from about 0.01 to 2 weight percent, and using as the catalyst $FeCl_3$ in an amount of from about 0.05 to 2 weight percent, the weights being calculated on benzoyl chloride used as the starting compound.

13. The process, as claimed in claim 12, wherein the catalyst is used in an amount of from about 0.01 to 1 weight percent and the cocatalyst is used in an amount corresponding to a sulfur content of about 0.05 to 0.5 weight percent.

* * * * *